United States Patent [19]
Harada et al.

[11] Patent Number: 5,696,301
[45] Date of Patent: Dec. 9, 1997

[54] PROCESS FOR PREPARING PROTOCATECHUALDEHYDE

[75] Inventors: Katsumasa Harada; Masashi Shirai; Toshio Furuya; Nobuyuki Kuroda, all of Yamaguchi, Japan

[73] Assignee: Ube Industries, Ltd., Yamaguchi, Japan

[21] Appl. No.: 787,583

[22] Filed: Jan. 22, 1997

[30] Foreign Application Priority Data

Jan. 23, 1996 [JP] Japan ................................ 8-009155
Jan. 23, 1996 [JP] Japan ................................ 8-009156

[51] Int. Cl.$^6$ .................... C07C 34/10; C07D 307/00; C07B 317/44
[52] U.S. Cl. ...................... 568/763; 546/434; 546/436
[58] Field of Search .................. 568/763, 715; 549/434, 436; 568/425

[56] References Cited

U.S. PATENT DOCUMENTS 5,420,308   5/1995   Andres .
5,525,739   6/1996   Andres .

OTHER PUBLICATIONS

Schiess etal., Formation of Substituted Benzocyclobutenes through Flash Vacuum Pyrolysis, Tet. Lett., vol. 23, No. 36, pp. 3669–3672, 1982.

Bich et al., Synthesis of 3,4–dihydroxy–2–methoxybenzaldehyde: The Use of Methylenedioxy as a Protecting Group, Aust. J. Chem., vol. 22, No. 7, pp. 1563–1568, 1969.

*Primary Examiner*—Jose G. Dees
*Assistant Examiner*—Karl J. Puttlitz
*Attorney, Agent, or Firm*—McAulay Fisher Nissen Goldberg & Kiel, LLP

[57] ABSTRACT

Protocatechualdehyde is prepared by the steps of reacting piperonyl dichloride with molecular chlorine in the presence of phosphorus trichloride, phosphorus pentachloride or sulfuryl chloride to prepare dichloropiperonylidene dichloride and hydrolyzing the dichloropiperonylidene dichloride. The piperonyl dichloride can be prepared by the reaction of piperonal with thionyl chloride in the presence of dimethylformamide.

9 Claims, No Drawings

PROCESS FOR PREPARING PROTOCATECHUALDEHYDE

FIELD OF THE INVENTION

The present invention relates to a process for preparing protocatechualdehyde. The protocatechualdehyde is of value as an intermediate compound for preparing known pharmaceutically active compounds and agricultural chemicals. Further, the protocatechualdehyde is employable for producing a microphotoresist and other material to be utilized for manufacture of electronic elements.

BACKGROUND OF THE INVENTION

Protocatechualdehyde has the following formula (a):

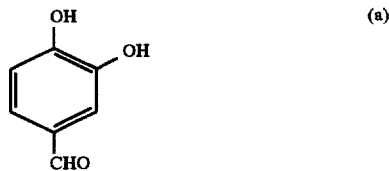

(a)

Heretofore, the protocatechualdehyde (i.e., 3,4-dihydroxybenzaldehyde) has been prepared by the steps of chlorinating piperonal (heliotropin), and hydrolyzing the chlorinated piperonal. In more detail, J. Chem. Soc., 93, 563–573 (1908) and Org. Syn., vol. 11, 549–550 describe a process (process 1) comprising the reaction of piperonal with phosphorus pentachloride and the hydrolysis of thus obtained tetrachlorinated product. J. Am. Chem. Soc., 52, 2988–2994 (1930) describes a process (process 2) comprising the reaction of piperonal with aluminum tribromide and the hydrolysis of the resulting product. DE 339945 describes a process (process 3) which comprises production of dichloropiperonyl chloride by reacting piperonal successively with thionyl chloride and molecular chlorine, and subsequent hydrolysis of the dichloropiperonyl chloride.

These known processes have disadvantageous features. For instance, the process 1 requires the use of a great amount of phosphorus pentachloride, i.e., five molar times as much as the molar amount of piperonal. The use of such a great amount of the phosphorus compound gives a by-produced phosphorus compound, which is troublesome in its discharge. The process 2 gives the desired product only in a low yield, and moreover the aluminum sometimes attaches to the resulting compound. Such by-product renders purity of the desired product lower. The process 3 gives 6-chloropiperonal having chlorine atom on its benzene ring as a main product, and give the desired product only in a low yield.

SUMMARY OF THE INVENTION

It is a main object of the present invention to provide a new industrially advantageous process for the preparation of protocatechualdehyde.

Particularly, the invention has an object to provide a process for preparing protocatechualdehyde in a higher yield and with little production of by-products.

The present invention provides a process for preparing protocatechualdehyde which comprises the steps of:

reacting piperonyl dichloride with molecular chlorine in the presence of a chlorine atom-containing compound selected from the group consisting of phosphorus trichloride, phosphorus pentachloride, and sulfuryl chloride, to prepare dichloropiperonylidene dichloride; and hydrolyzing the dichloropiperonylidene dichloride.

The invention further provides a process for preparing protocatechualdehyde which comprises the steps of:

reacting piperonal with thionyl chloride in the presence of dimethylformamide to prepare piperonyl dichloride;

reacting the piperonyl dichloride with molecular chlorine in the presence of a chlorine atom-containing compound selected from the group consisting of phosphorus trichloride, phosphorus pentachloride, and sulfuryl chloride, to prepare dichloropiperonylidene dichloride; and hydrolyzing the dichloropiperonylidene dichloride.

DETAILED DESCRIPTION OF INVENTION

According to the invention, the protocatechualdehyde can be prepared from piperonyl dichloride. The piperonyl dichloride can be prepared by chlorinating heliotropin (piperonal) in a known way, such as that described in J. Chem. Soc., 93, 563–573 (1908). The chlorination can be done using phosphorus pentachloride of a stoichiometric amount. The piperonal and piperonyl dichloride are represented by the following formulas (b) and (c), respectively.

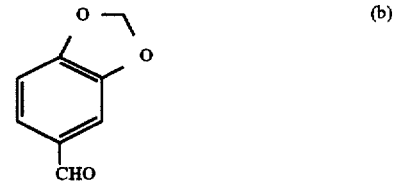

(b)

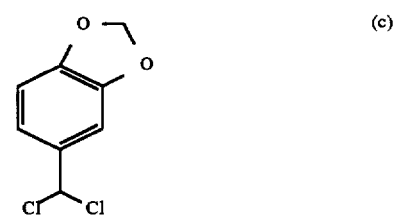

(c)

In more detail, in the chlorination of piperonal, piperonal and thionyl chloride are reacted at 20°–100° C. in the presence of a catalytic amount of dimethylformamide (i.e., N,N-dimethylformamide). The dimethylformamide my be employed in an amount of 1 to 20 wt. %, preferably 1 to 10 wt. %, based on the amount of piperonal. In the absence of dimethylformamide, the reaction almost does not proceed. The thionyl chloride may be employed in an amount of 1 to 2 moles, preferably 1 to 1.2 moles, per one mole of piperonal. The reaction pressure is not limitative, but the reaction is generally performed under atmospheric pressure. Such reaction gives the desired piperonyl dichloride in a quantitative yield.

The piperonyl dichloride is then chlorinated by a molecular chlorine in the presence of a chlorine atom-containing compound such as phosphorus trichloride, phosphorus pentachloride or sulfuryl chloride, to give dichloropiperonylidene dichloride having the following formula (d):

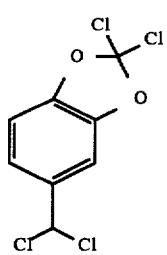

(d)

The chlorination of piperonyl dichloride can be performed in the presence of the chlorine atom-containing compound in an amount of 0.05 to 1.5 moles, preferably 0.1 to 1 mole, based on one mole of the piperonyl dichloride (or the piperonal). If the amount of the chlorine atom-containing compound is less than the lower limit, not a small amount of by-products in which the benzene ring of piperonyl dichloride is chlorinated are produced. Among phosphorus trichloride, phosphorus pentachloride and sulfuryl chloride, phosphorus trichloride is preferably employed in industry because it is easily handled and is not expensive.

The chlorination of piperonyl dichloride can be performed using a molecular chlorine in an amount of 1 to moles, preferably 1 to 5 moles, based on one mole of the piperonyl dichloride. If the amount of molecular chlorine is less than the lower limit, the reaction proceeds too slowly. If the amount of molecular chlorine exceeds the upper limit, not a small amount of by-products in which the benzene ring of piperonyl dichloride is chlorinated are produced.

The chlorination of piperonyl dichloride can be performed in a mixture of a solution of piperonyl dichloride (which has been obtained by chlorination of piperonal), a solvent, and a chlorine atom-containing compound such as phosphorus trichloride, phosphorus pentachloride, or sulfuryl chloride. In the reaction, a molecular chlorine such as gaseous chlorine is passed through the mixture in a reaction vessel kept at generally 25° to 150° C., preferably 25° to 100° C. The reaction pressure is not limitative, but the reaction is generally performed under atmospheric pressure. The molecular chlorine such as gaseous chlorine can be supplied after diluting it with an inert gas such as gaseous nitrogen.

The solvent employable for the chlorination reaction should dissolve piperonyl dichloride and preferably is inert to the chlorine atom-containing compound as well as to the molecular chlorine. Examples of the employable solvents include (1) aromatic hydrocarbons such as benzene, toluene, xylene, ethylbenzene and chlorobenzene; (2) halogenated aliphatic hydrocarbons such as carbon tetrachloride, chloroform, methylene chloride and 1,2-dichloroethane; (3) aliphatic hydrocarbons having no halogen atoms such as n-hexane, n-heptane, n-octane, n-decane, cyclohexane, cycloheptane and cyclooctane; (4) ethers such as diethyl ether, diisopropyl ether, tetrahydrofuran, and dioxane; and (5) esters such as ethyl acetate and butyl acetate. The aromatic hydrocarbons, halogenated aliphatic hydrocarbons and esters are preferred.

The solvent may be employed in an amount of 0.1 to 5 L, preferably 0.1 to 3 L, per one mole of the piperonyl dichloride (or the piperonal).

The dichloropiperonylidene dichloride is then hydrolyzed to give the desired protocatechualdehyde of the aforementioned formula (a).

The hydrolysis can be performed by adding water to the reaction mixture of dichloropiperonylidene dichloride. The amount of water generally is in a range of 0.1 to 5 L, preferably 0.1 to 3 L, based on one mole of the dichloropiperonylidene dichloride or the starting piperonal. The hydrolysis reaction is generally performed at 0° to 100° C., preferably 0° to 80° C. under atmospheric pressure.

Thus produced protocatechualdehyde is then recovered and purified by known ways, for instance, by extraction and crystallization.

The present invention is further described by the following examples. In the following examples, the yield of protocatechualdehyde is calculated on the basis of the amount of piperonal employed.

EXAMPLE 1

In a glass reaction vessel (100 mL volume) equipped with a stirrer and a dropping funnel, 20 g (0.13 mol) of piperonal, 0.85 g of dimethylformamide, and 16.96 g (0.14 mol) of thionyl chloride were placed at room temperature in a stream of gaseous argon. The resulting mixture was heated to 50° C. under stirring. The mixture was stirred two hours at the same temperature under atmospheric pressure and further stirred one hour under reduced pressure. In the reaction mixture, piperonyl dichloride was produced in a quantitative yield.

Subsequently, 100 mL of toluene and 3.67 g (0.027 mol) of phosphorus trichloride ($PCl_3$) were added to the reaction mixture. Into the resulting mixture was blown gaseous chlorine (0.26 mol) at 50° C. for the period of 2 hours. The mixture was cooled to a temperature below 20° C., and 40 ml of water was added to the cooled mixture. The mixture was then stirred for one hour for performing hydrolysis. The reaction was performed under atmospheric pressure.

After the reaction was complete, the precipitated solid was collected by filtration, and the aqueous filtrate was subjected to extraction with ethyl acetate. The collected solid and the ethyl acetate extract were combined. The combined mixture was washed with an aqueous saturated sodium chloride solution and then dried over anhydrous sodium sulfate. The dried mixture was placed under reduced pressure to distill off the solvent. The precipitated crystalline product was collected by filtration and dried under reduced pressure at room temperature, to give 15.48 g (yield: 84%) of protocatechualdehyde.

COMPARISON EXAMPLE 1

The procedures of Example 1 were repeated except for employing no dimethylformamide. In the procedures, the first chlorination appeared not to proceed. The desired protocatechualdehyde was not obtained, and a by-product of 6-chloropiperonal was recovered in a 70% yield.

EXAMPLE 2

The procedures of Example 1 were repeated except for replacing the phosphorus trichloride with phosphorus pentachloride ($PCl_5$, 0.027 mol). There was obtained 15.45 g (yield: 86%) of protocatechualdehyde.

EXAMPLE 3

The procedures of Example 1 were repeated except for replacing the phosphorus trichloride with sulfuryl chloride ($SO_2Cl_2$, 0.027 mol). There was obtained 14.37 g (yield: 80%) of protocatechualdehyde.

EXAMPLE 4

The procedures of Example 1 were repeated except for replacing the phosphorus trichloride with sulfuryl chloride ($SO_2Cl_2$, 0.027 mol) and further replacing the toluene with carbon tetrachloride (100 mL). There was obtained 14.73 g (yield: 82%) of protocatechualdehyde.

EXAMPLES 5 TO 7

The procedures of Example 1 were repeated except for replacing the toluene with the solvent set forth in Table 1, and altering the period of gaseous chlorine-blowing as set forth in Table 1. The results of Examples 5 to 7 are set forth in Table 1. The results of Examples 1 to 4 are also set forth in Table 1.

TABLE 1

| Example No. | Solvent | Chlorine Compound | Period of Chlorination (hr) | Yield of Protocatechualdehyde (%) |
|---|---|---|---|---|
| 1 | toluene | $PCl_3$ | 2 | 84 |
| 2 | toluene | $PCl_5$ | 2 | 86 |
| 3 | toluene | $SO_2Cl_2$ | 2 | 80 |
| 4 | $CCl_4$ | $SO_2Cl_2$ | 2 | 82 |
| 5 | $CCl_4$ | $PCl_3$ | 5 | 80 |
| 6 | $CH_3COOC_2H_5$ | $PCl_3$ | 1 | 79 |
| 7 | $ClCH_2CH_2Cl$ | $PCl_3$ | 3 | 64 |

What is claimed is:

1. A process for preparing protocatechualdehyde which comprises the steps of:
    reacting piperonyl dichloride with molecular chlorine in the presence of a chlorine atom-containing compound selected from the group consisting of phosphorus trichloride, phosphorus pentachloride, and sulfuryl chloride, to prepare dichloropiperonylidene dichloride; and
    hydrolyzing the dichloropiperonylidene dichloride.

2. The process of claim 1, wherein the step of reacting piperonyl dichloride with molecular chlorine is performed in a solvent.

3. The process of claim 1, wherein the molecular chlorine is gaseous chlorine.

4. The process of claim 1, wherein the step of reacting piperonyl dichloride with molecular chlorine is performed in a solvent selected from the group consisting of aromatic hydrocarbons, halogenated aliphatic hydrocarbons, aliphatic hydrocarbons having no halogen atoms, ethers, and esters.

5. A process for preparing protocatechualdehyde which comprises the steps of:.
    reacting piperonal with thionyl chloride in the presence of dimethylformamide to prepare piperonyl dichloride;
    reacting the piperonyl dichloride with molecular chlorine in the presence of a chlorine atom-containing compound selected from the group consisting of phosphorus trichloride, phosphorus pentachloride, and sulfuryl chloride, to prepare dichloropiperonylidene dichloride; and
    hydrolyzing the dichloropiperonylidene dichloride.

6. The process of claim 5, wherein the step of reacting piperonyl dichloride with molecular chlorine is performed in a solvent.

7. The process of claim 5, wherein the molecular chlorine is gaseous chlorine.

8. The process of claim 5, wherein the step of reacting piperonal with thionyl chloride and the step of reacting the piperonyl dichloride with molecular chlorine are conducted successively without isolating the piperonyl dichloride produced in the former step.

9. The process of claim 5, wherein the step of reacting piperonyl dichloride with molecular chlorine is performed in a solvent selected from the group consisting of aromatic hydrocarbons, halogenated aliphatic hydrocarbons, aliphatic hydrocarbons having no halogen atoms, ethers, and esters.

* * * * *